(12) United States Patent
Boehringer et al.

(10) Patent No.: US 6,228,056 B1
(45) Date of Patent: May 8, 2001

(54) INTERMITTENT REGULATOR

(75) Inventors: John R. Boehringer, Wynnewood; John Karpowicz, Chester Springs; Michael I. Hegedus, Royersford; Anthony Turchi, Collegeville, all of PA (US)

(73) Assignee: Boehringer Laboratories, Inc., Norristown, PA (US)

( * ) Notice: Subject to any disclaimer, the term of this patent is extended or adjusted under 35 U.S.C. 154(b) by 0 days.

(21) Appl. No.: 09/334,240

(22) Filed: Jun. 16, 1999

(51) Int. Cl.$^7$ ................................................. A61M 1/00
(52) U.S. Cl. ...................................................... 604/118
(58) Field of Search .................. 604/118–123, 131–136, 604/140–144, 146–147, 149, 151–154

(56) References Cited

U.S. PATENT DOCUMENTS 4,662,829 * 5/1987 Nehring ................................ 417/395
5,265,639 * 11/1993 Tobia et al. .......................... 137/103

* cited by examiner

Primary Examiner—Sharon Kennedy
Assistant Examiner—Ann Y. Lam
(74) Attorney, Agent, or Firm—Paul & Paul

(57) ABSTRACT

An intermittent regulator is provided in which the regulator alternates between supplying partial vacuum to a patient for withdrawing fluids from the body of a patient, and supplying atmosphere to a patient, at a selected intermittent rate, that is adjustable upon adjusting a timing mechanism. The timing mechanism is isolated from communicating with the vacuum being drawn from a patient, separating the regulator into a "wet" side and a "dry" side. The regulator includes a piston and spool, each having magnets therein, whereby intermittent motion of the piston controls the motion of the spool and which thereby controls the opening of ports for delivery/non-delivery of vacuum to a patient. An alternative embodiment has porting for sensing occlusion in the patient line and converting the regulator from a continuous-on operation to an intermittent operation. An alternative embodiment has separate air inlet and outlet conduits to atmosphere from the "dry" side of the regulator.

18 Claims, 5 Drawing Sheets

INTERMITTENT REGULATOR

BACKGROUND OF THE INVENTION

Figure 1:
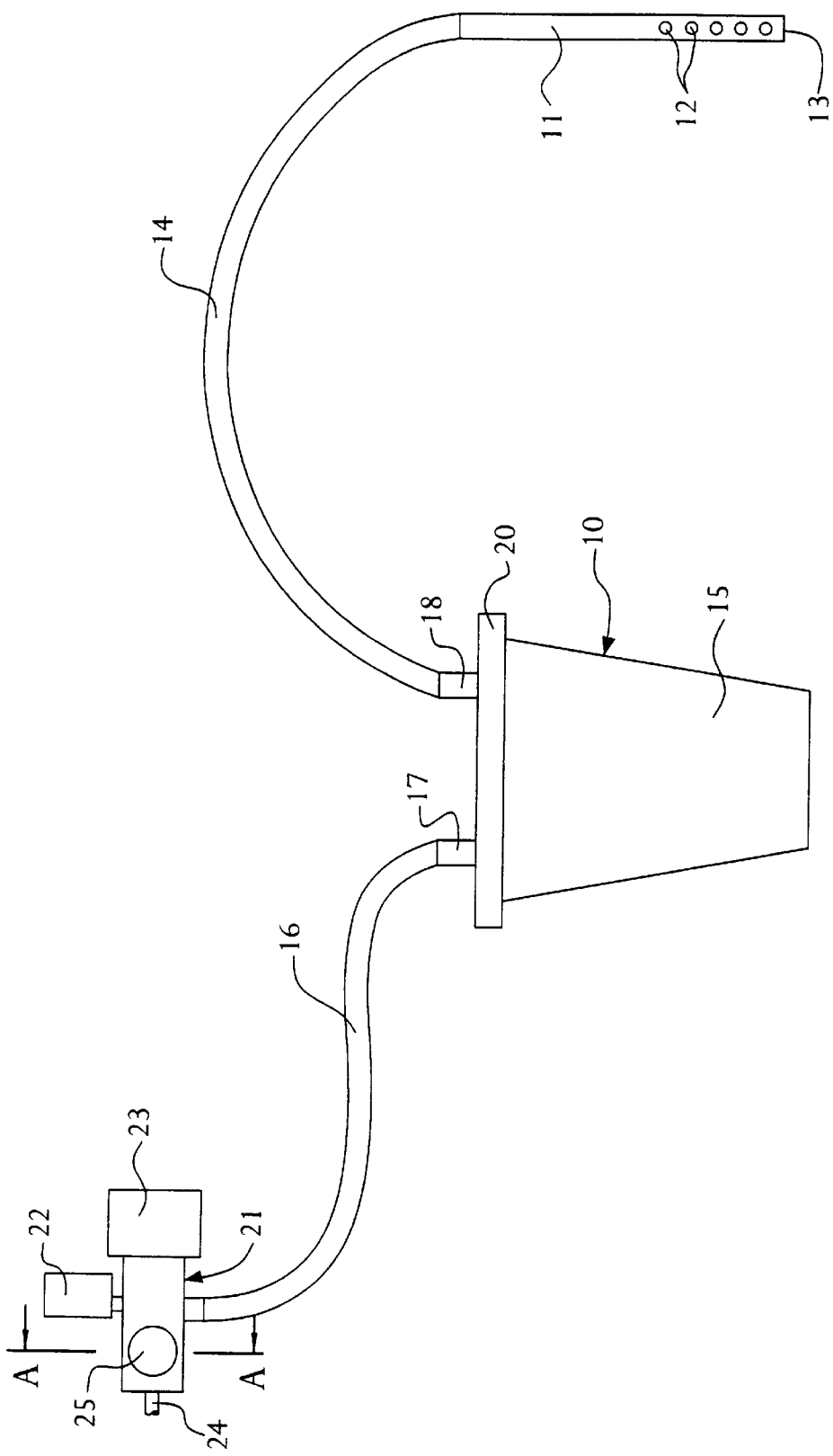

In the art of regulators, and more particularly in the art of intermittent regulators, it is known to provide suction regulation for physicians and other medical personnel, to provide such clinicians the advantage of intermitting suction capability, in one generally compact unit. Such intermittent regulators supply vacuum and atmospheric pressure alternately.

Typically, in evacuating fluids from the body, such as but not limited to, evacuating fluid from the stomach area, it is possible for the suction catheter to engage the stomach wall, thereby occluding the inlet of the suction catheter. In such event, it is desirable to have the vacuum draw of fluid from the stomach become discontinuous, to free the catheter from sucking against the stomach wall and damaging the stomach lining.

It is also common for debris in the stomach area to occlude the inlet ports of a catheter and thereby restrict or impede fluid flow. Periodic and regular relief of suction pressure to atmosphere will discourage debris accumulation on catheter inlets.

Because it is not always readily apparent when such occlusion occurs, suction regulators can be operated on a substantially ongoing or intermittent manner by periodic regular cycling of vacuum on and venting to atmosphere of the collection circuit.

In other instances, intermittent regulators are provided that may be set to operate in either a continuously intermittent (on/off, on/off, on/off, etc.) mode, or may be capable of being set to optionally operate in a constant-on or in a constant-off mode.

It is also known that because of the nature of fluids being withdrawn from the body of a patient, it is necessary to provide regulators that are capable of being sterilized between uses.

SUMMARY OF INVENTION

The present invention is directed to providing an intermittent regulator that is magnetically operable.

The present invention is also directed to providing an intermittent regulator that has a control means for controlling the intermitting time cycle, but wherein the control means is isolated from body fluids that are delivered to the regulator from the body of a patient.

It is another object of this invention to provide an intermittent regulator in which solid particles entrained in the fluid being withdrawn from a body can be severed to encourage passage through the regulator to avoid jamming the operation of the regulator.

It is a further object of this invention to provide a regulator with a visual indication of the operating mode thereof.

It is yet another object of this invention to provide an intermittent regulator with one or more stops for indicating the position or mode of operation of components of the regulator, as well as to provide for overriding the operation of the regulator via manual action by an operator.

It is another object of the invention to provide a near constant ratio of on/off operation of the regulator, even with variation in supply of vacuum to the regulator. It is also an object of this invention to provide for independent adjustment of the on/off times.

Other objects of the present invention will become readily apparent from a reading of the following brief descriptions of the drawing figures, the detailed descriptions of the preferred embodiments, and the appended claims.

BRIEF DESCRIPTION OF THE DRAWING FIGURES

FIG. 1 is a schematic illustration of a system for withdrawing body fluids from a patient, including a drainage tube, a container for receiving fluids withdrawn from the body of a patient, and a vacuum regulator of the type of this invention, incorporating the intermitting feature of this invention, which regulator is adapted for connection to a source of hospital vacuum or the like.

Figure 2:
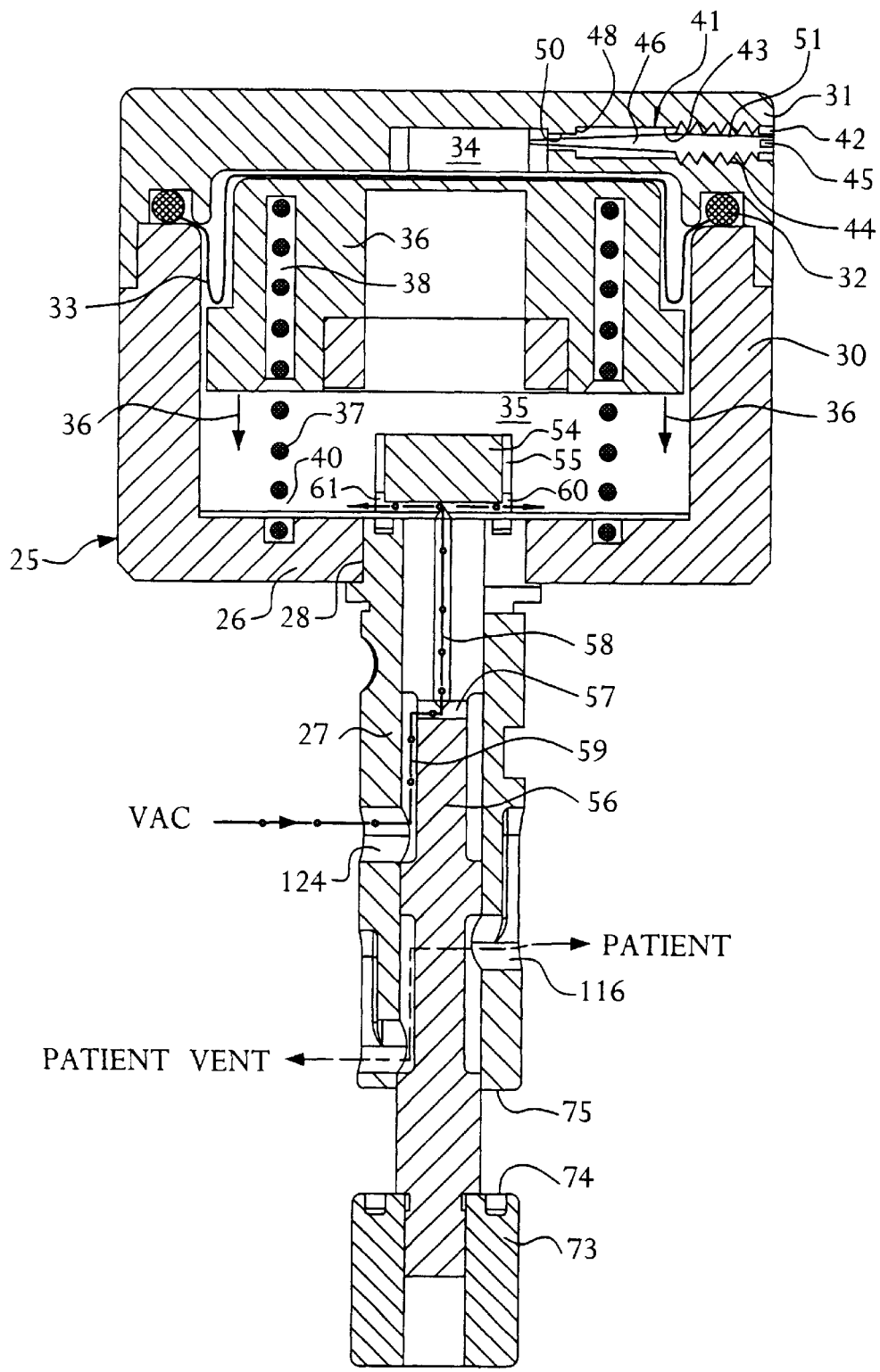

FIG. 2 is a cross-sectional view taken through the intermittent regulator housing along the line A—A of FIG. 1, and wherein it is shown that a diaphragm separates the housing between a dry side where the timing mechanism is situated, and a wet side, with a piston disposed below the diaphragm and moveable from the position for the piston that is shown in FIG. 2, vertically downwardly, as dictated by a vacuum draw through the housing surrounding the vertically movable spool, for evacuating the zone beneath the piston. In the illustration of FIG. 2, the connection to the patient is shown in a venting mode.

Figure 3:
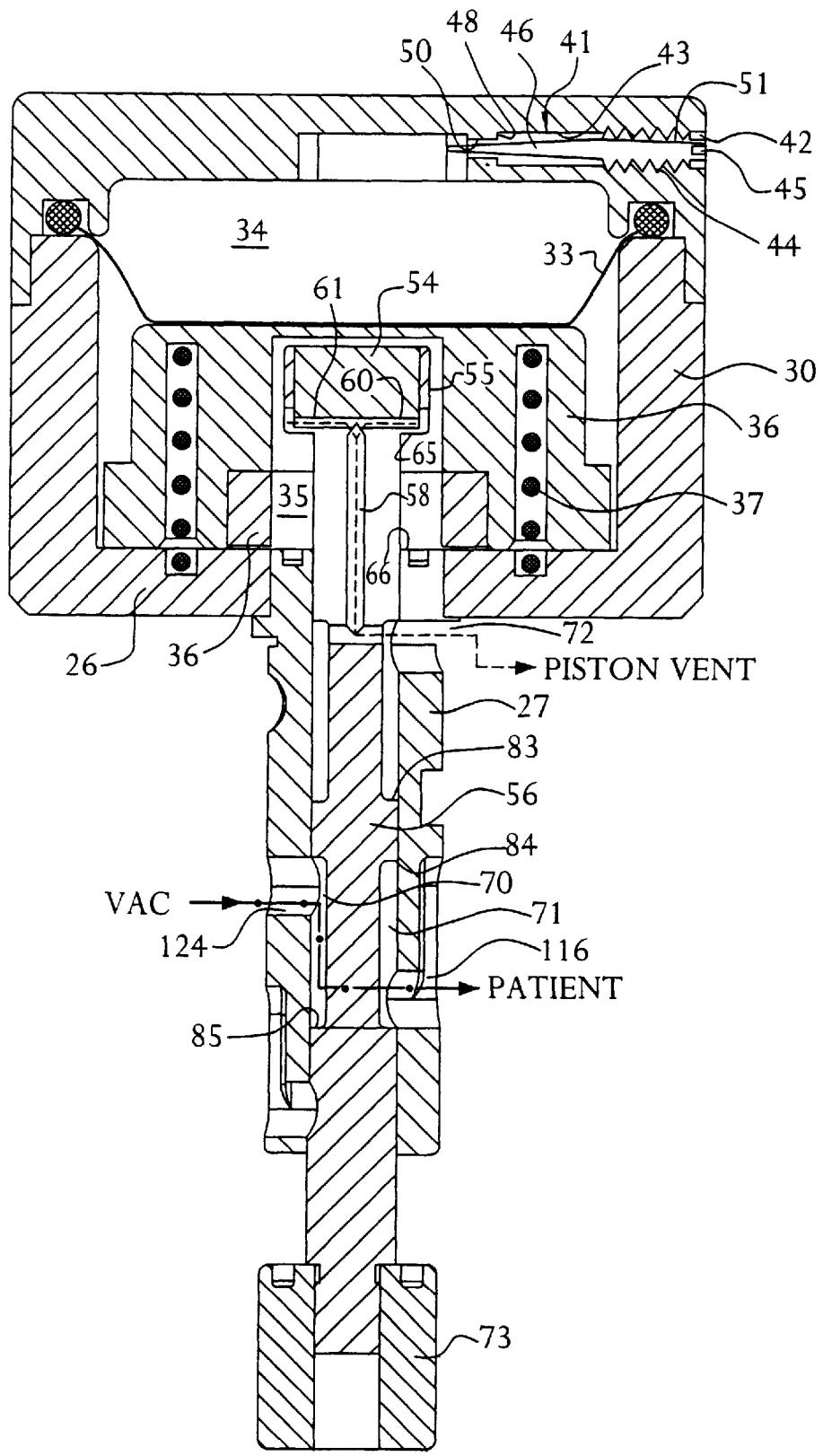

FIG. 3 is a cross-sectional view taken generally along the line A—A of FIG. 1, similar to that of FIG. 2, but showing the regulator adapted for connection to a source of partial vacuum, for delivery of said partial vacuum to a patient, via a conduit in a vertically movable spool, and wherein the housing of the regulator shows a vacuum-operable piston in the piston vent mode, in which atmospheric air may enter the housing on the dry side of the diaphragm, past the timing mechanism, and with the piston withdrawn downwardly.

Figure 4:
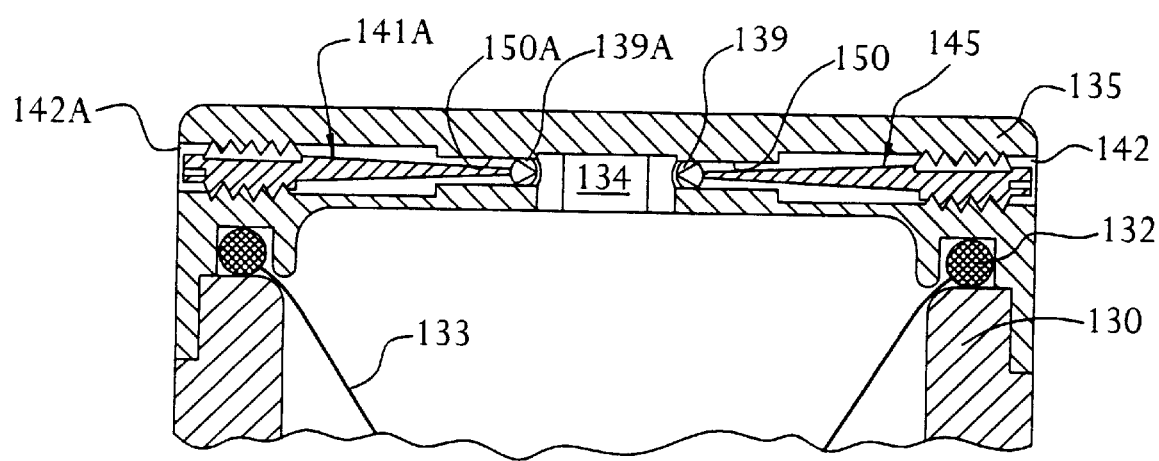

FIG. 4 is a fragmentary cross-sectional view similar to that of each of FIGS. 2 and 3, but wherein independent timing mechanisms are provided for inflow and outflow of air into the regulator housing, on the dry side of the diaphragm.

Figure 5:
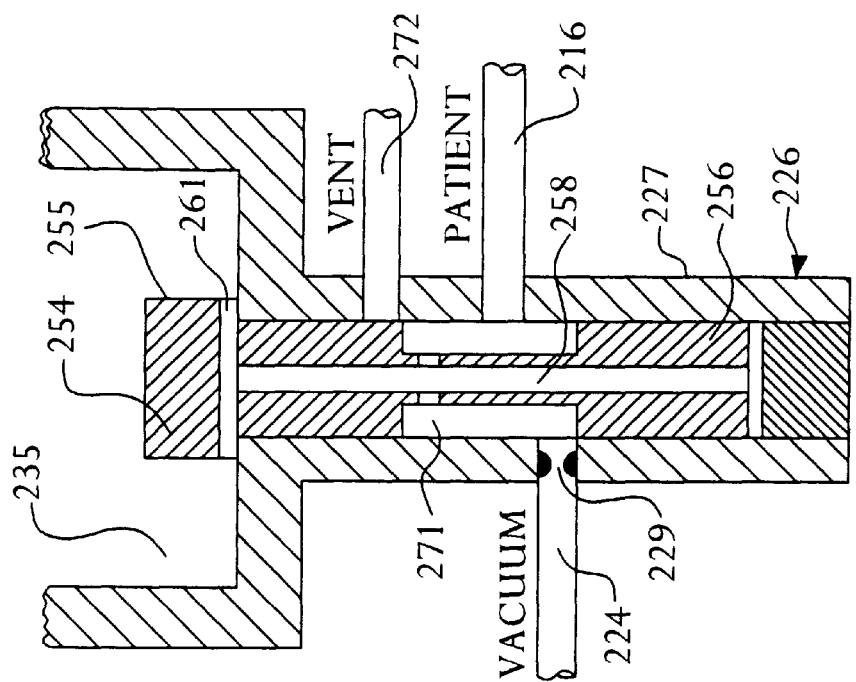
Figure 6:
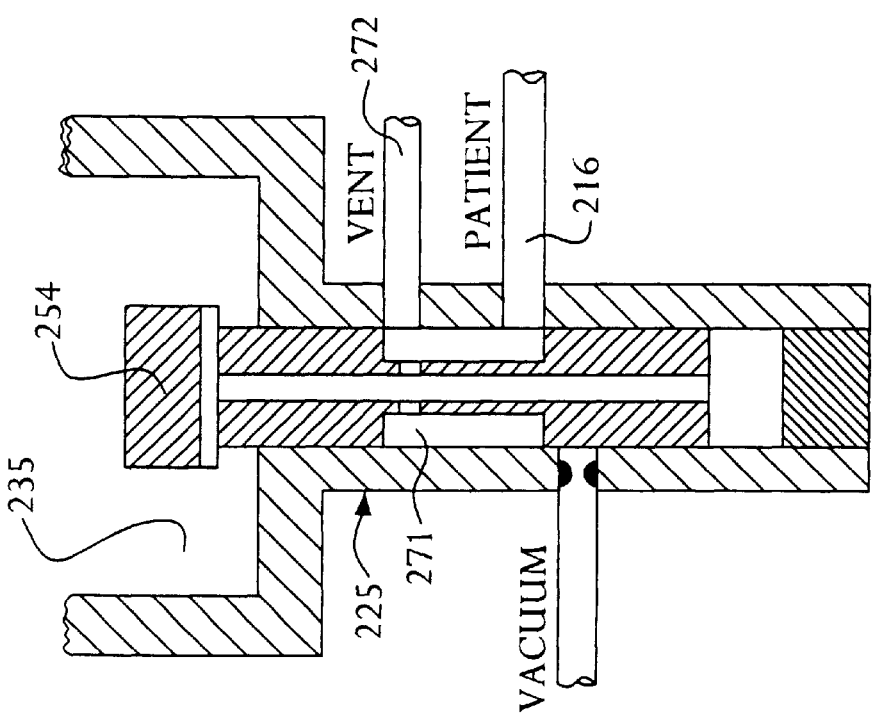

FIGS. 5 and 6 illustrate schematically, in fragmentary vertical cross-section, a modified valve arrangement to that shown in FIGS. 2 and 3, in which evacuation of the piston chamber occurs at the same time that the patient is evacuated, as in FIG. 5, but wherein, in the event of occlusion of the patient's catheter, the vacuum will increase in the patient line and the piston chamber will see increased vacuum and shift the spool up to the intermitting mode in which the patient line and piston chamber are both vented as shown in FIG. 6.

DETAILED DESCRIPTION OF THE PREFERRED EMBODIMENTS

Referring now to the drawings in detail, reference is first made to FIG. 1, wherein a patient drainage system is generally indicated by the numeral 10, as including a gastrointestinal drainage tube 11, having a plurality of inlet openings 12 thereof, and generally an inlet at the end 13 thereof, connected to a patient connection means, generally of the tube type, 14, which, in turn, is connected to a container 15, for emptying body fluids such as liquid, blood, sputum, any entrained solid particles and the like, water, etc., into the collection container 15.

Another leg of patient connection tubing 16 is provided, for drawing a partial vacuum from the container 15, via tubing connections 17, 18 carried by the cap 20 of the container 15, as shown. The tubing 16 is connected to an intermittent vacuum regulator 21 that, in turn, carries a gauge 22 and an adjustment knob 23 thereon, and which is connected at 24 to a source of partial vacuum, such as hospital line vacuum or the like. The intermittent module 25 contains the piston and spool with associated piston magnet, spool magnet, stops, timing mechanism, etc. associated therewith.

Referring now to FIG. 2, the intermittent module 25 will now be described.

The module 25 includes an upper module housing component 26 and a lower module housing component 27. The lower housing component 27 will generally be disposed within the vacuum regulator 21, with suitable porting provided to various components of the housing 27. For example, the partial vacuum supply line 24 and the patient connection line 16 are shown communicating with their respective ports 124 and 116 in FIG. 2.

The housing component 26 receives the upper end of the housing component 27 therein, at its lower end, as shown at 28, to affix the two housing components 26 and 27 together.

The housing component 26 includes a generally cylindrical wall 30 against which is secured an end cap 31, by suitable screws or other fasteners, not shown.

Sandwiched between the end cap 31 and the cylindrical wall 30 is the annular bead 32 of a diaphragm 33. The diaphragm 33 is of the flexible, elastomeric, or otherwise stretchable type, being comprised of rubber, neoprene, or other suitable materials. The diaphragm 33 is connected to the bead 32, and serves to separate the "dry" zone 34 above the diaphragm 33 from the "wet" zone 35 below the diaphragm 33.

A vertically moveable piston 36 is disposed inside the cylindrical portion 30, capable of movement from the position shown in FIG. 2, vertically downwardly in the direction of the arrows 36 shown in FIG. 2, against the upwardly urging force supplied by a generally cylindrical compression spring 37, as shown, seated at its upper end in annulus 38, and at its lower end in annulus 40.

A timing circuit or mechanism 41 is provided, communicating between atmospheric air present at the inlet 42 of a bore 43 and the dry zone 34.

The timing mechanism 41 is in threaded engagement at 44 with the interior wall of the bore 43, and is adjustably positionable therein, by engaging a screwdriver or the like in a slot 45 at the outer end of the mechanism 41, for turning the mechanism and thereby causing a taper 46 carried thereby to move leftwardly or rightwardly depending upon the direction in which the mechanism 41 is turned. Such leftward or rightward movement of the taper 46 will cause the same to interact with a seat 48 of a bore 50 to be, respectively, more open or more closed, thereby adjusting the cross-sectional area between the taper 46 and bore 50, to thereby regulate the flow rate of air passing between the zone 34 and the zone 42, through the seat created by the taper 46 and bore 50, and through a longitudinally cut passage conduit 51 or the like extending through the timing mechanism 41.

It is thus seen that the timing mechanism 41 can be used to adjust the opening between the taper 46 and the bore 50, and thereby regulate the exchange of air between the zones 34 and 42, thereby regulating the rate of intermittent motion of the piston 36 between its up position illustrated in FIG. 2 and its down position illustrated in FIG. 3. Such regulation of the intermittent motion of the piston 36, will likewise regulate the upward and downward motion of the spool carried within the housing portion 27 as will be discussed hereinafter, to, in turn, regulate the delivery or non-delivery of partial vacuum to a patient. In the case of non-delivery of partial vacuum to a patient, the patient will be vented to atmosphere as shown at the lower end of FIG. 2. The timing mechanism as described above adjusts the flow rate of air into and out of space 34. This arrangement provides for instantaneous adjustments of the times for delivery and non-delivery of vacuum to the patient. At times, it may be desirable to independently control the times of delivery and non-delivery of vacuum to a patient, as will be addressed hereinafter with reference to an alternative embodiment illustrated in FIG. 4.

The piston 36 carries a permanent magnet 53 therein, for interaction with a permanent magnet 54 carried in a cylindrical stop 55 at the upper end of the vertically moveable spindle 56 that is, in turn, carried within the housing component 27 as shown.

When vacuum is applied at 124, it draws via conduit line 59, 57 and 58 in spool 56, and via conduit lines 60 and 61 as shown by the arrows extending through conduits 60 and 61. Thus, in the positions of the piston 36 and spool 56 as shown in FIG. 2, the application of vacuum at location 124 will apply such vacuum to zone 35 beneath the piston 36, causing the piston 36 to be drawn vertically downwardly in the direction of the arrows 36 against the force applied by the compression spring 37, thereby drawing atmospheric air across the timing mechanism 41 into the zone 34, at a flow rate determined by the setting of the timing mechanism 41, such that atmospheric air can enter the dry side 34 of the diaphragm 33.

As the magnet 53 begins to approach the magnet 54, the electromagnetic interacting forces will tend to resist the further downward movement of the piston 36 somewhat, but the vacuum draw provided at 124 will be sufficiently large to overcome any magnetic resistance thereto, so that the piston 36 will continue to be drawn downwardly. At the point that the magnet 53 passes over the approximate center of the magnet 54, the magnetic polarity will cause the magnet 54 to be pushed upwardly relative to the magnet 36, thereby drawing upwardly the spool 56 in which the magnet 54 is carried, at its upper end. The spool 56 will thus shift from the downward position therefor shown in FIG. 2, to the upward position therefor shown in FIG. 3, such that the cylindrical portion 55 will be moved upwardly as shown in FIG. 3, whereby the stop 65 at the lower end of cylindrical portion 55, which limits the vertical downward motion of the spool 56 when it is in the position shown in FIG. 2 by engaging against the upper end 66 of the housing portion 27, will now be spaced from the upper end 66 of the housing portion 27 as shown in FIG. 3.

In the position for the spool 56 as shown in FIG. 3, vacuum applied at 124 enters conduit 70, which communicates with conduit 71 and draws via patient connection line 116, as shown, to draw body fluids from a patient through line 14 to container 15. In the position for the spool illustrated in FIG. 3, the "wet" zone 35 beneath the diaphragm 33 is free to vent to atmosphere via conduits 60, 61 and 58, via vent 72.

It will be noted that the spool 56 carries a lower stop 73 at its lower end, such that a stop surface 74 can engage against a lower surface 75 on the spool housing portion 27, to limit the upward movement of the spool. It is thus seen that the surfaces 74 and 65 at lower and upper ends of the spool 56, respectively, serve to provide stops limiting the back-and-forth, or upward and downward movement of the spool 56.

It will be apparent that the stops can be adjustably positionable, if desired, although the same is not shown. Such adjustment can be provided by making the cylindrical portion 55 at the upper end of the stop, and its lower end 65, threadingly adjustable on the upper end of the spool 56, and by making the stop 73 at the lower end threadingly adjustable on the lower end of the spool 56.

It is thus seen that, by separating the timing mechanism 41 from that side of the vacuum draw which is connected to a patient, via the separating diaphragm 33, proteinaceous matter that might become entrained along with fluids being drawn from the patient and drawn into housing component 27 is isolated from the timing mechanism, such that the timing mechanism 41 will not become clogged by matter present in the timing mechanism.

It will also be noted that circumferential edges such as but not limited to those 83, 84 and 85 of the spool will preferably be sharp, so as to provide a means for cutting against and severing solid particles, such as proteinaceous matter into smaller particles as spool 56 moves upwardly and downwardly, to thereby reduce the prospects of clogging within the housing portions 26, 27.

Additionally, the protruding stop 73 allows a manual override via the intervention of a medical practitioner, in the event of unusual activity, such as jamming or the like. Also, the stop 73 may provide a visual indication of the position of the spool. For example, the stop 73 may be provided with a particularly noticeable color, striping, or other visual indication to readily indicate the position of the spool either in a vacuum-to-patient mode or in a vacuum-not-to-patient mode.

Thus, it is seen that timing of the regulator is achieved by varying the air flow into the dry side 34 of the diaphragm 33, through the needle mechanism 41. In clinical applications, the times are generally set for intermittent regulators at 8–10 seconds off and 16–20 seconds on. These times have become an acceptable clinical practice. It is possible that these times are long enough to provide a significant volume of fluid to be collected, precluding a premature shutoff and short enough so that the device can be observed by the nursing staff as acceptably working or cycling.

The ratio of times is thus accepted as being nominally two to one of "on" to "off" time. This requirement can be complicated with variation in hospital suction supply levels.

The intermitting regulator of this invention will maintain a consistent ratio of times over a supply variation of 300–600 mm Hg. It is recognized that the times will be affected, but their relationship to each other will be consistent. The total cycle time can be adjusted by adjustment of the needle valve and it is recognized that doing so will simultaneously adjust both the on and off times.

The effect of fluid flow across the needle valve mechanism 41 as supply pressures change is as follows, and operates on the assumption that the air in the dry chamber 34 is incompressible. When supply vacuum is increased, it is expected that the vacuum can draw the piston down faster and thus the time when vacuum is not applied to the patient, is reduced. As the valve shifts, supply pressure is vented and the spring returns the piston to the upward position illustrated in FIG. 3. Since the valve will shift at the same location in the body of the device, irrespective of supply vacuum, the spring urges the piston upwardly, forcing air out through the needle valve 46 of the timing mechanism 41. In theory, this would suggest that as supply vacuum increases, patient "off" times would decrease and patient "on" times would be constant. This would result in an increase in the "on" to "off" ratio.

In reality, however, the air in the dry chamber is not incompressible. The air expands when vacuum is applied and compresses as the spring is urging the piston upwardly. The expansion of air can be controlled to very precise levels by the volume established by the shape of the parts and the "tank" volume that is subsequently provided. The larger the initial or "tank" volume, the more expansion and compression there will be of the "tank" air. The key element that affects timing is that the lower the supply vacuum, the slower the piston travels and the more air comes through the valve. As supply vacuum is increased, the expansion of the residual air occurs faster than air can flow in through the valve. On the subsequent venting step, the piston has less air to move through the orifice and the cycle is shorter. The net result is that increasing the supply vacuum shortens both the vacuum "on" and "off" times, thus maintaining a consistent ratio. The degree of shortening is adjustable to some degree by varying a "tank" volume. The "tank" volume can be made so large as to eliminate the need for a needle valve 46 altogether. The cycling would thus be based purely on expansion of air in the "tank." However, by the use of the timing mechanisms, it is possible to enable adjustments in the time cycle.

Thus, the ends of the invention, including the avoidance of damage to the tissue of a patient is avoided or minimized, by preventing adherence of a suction catheter, tube or the like to the wall of a stomach or other tissue of a patient, by interrupting the draw of vacuum against such tissue, at definite time intervals.

With reference now to FIG. 4, it will be seen that it is possible, in the embodiment of FIG. 4, to independently control the "on" and "off" times discussed above, when it may be desirable to do so. Such independent control can be achieved by duplicating the valve arrangement of FIGS. 2 and 3, and incorporating one-way valves in such a manner as to permit inflow through one flow control and outflow through the other flow control. In FIG. 4, the cylindrical wall 130 of the housing and the end cap 131 clamp bead 132 of the diaphragm 133 therebetween, separating outer zones 142 and 142A from the inner zone 134 on the dry side of the diaphragm 133, generally similar to the arrangement of FIGS. 2 and 3. An inflow timing mechanism 141 allows for passage of air leftwardly as shown in FIG. 4, from atmosphere, to zone 134. A similarly configured timing mechanism 141A allows for passage of air outwardly, from the dry zone 134, across the timing mechanism 141A, as with the embodiments of FIGS. 2 and 3, but leftwardly as shown in the embodiment of FIG. 4. The timing mechanism 141 is provided with a one-way valve 139, which may be of the flapper valve type, to open when air moves thereacross in a leftward direction, but to close by having its upper and lower split halves seal against the bore 150, as shown, preventing air from the dry zone 134 from escaping rightwardly across the timing mechanism 141, with the flapper valve 139 opposing the same, in sealed engagement against the bore 150. However, discharge of air from the zone 134 leftwardly, to the zone 142A, can occur by passage of air around the flapper valve 134A, causing its halves to come together, opening up the seal between those flapper valve halves and bore 150A, thereby allowing the passage of air leftwardly across the timing mechanism 141A.

With reference now to FIGS. 5 and 6, it will be seen that there is taught a modified venting arrangement which enables the operation of a "smart" intermitting regulator. In the embodiment of FIGS. 5 and 6, the various components are generally similar to the corresponding components in the embodiment of FIGS. 2 and 3, including a housing portion 227 of a housing component 226, with a patient connection line 216 and a connection 224 to a source of partial vacuum, and with a vent 272, as shown. The piston, diaphragm, and spring arrangement are like those shown for the embodiment of FIGS. 2 and 3 and are not duplicated herein in the embodiment of FIGS. 5 and 6. A moveable spindle 256 is disposed within the housing portion 226, for vertical movement therein between the positions therefor shown in FIGS. 5 and 6. Conduit lines 258 and 261 and conduit 271 operate in the manner of corresponding conduit lines for the embodiment of FIGS. 2 and 3. Similarly, a magnet 254 is provided in a cylindrical stop 255, and operates to interact with a magnet carried by the piston (not shown) also in the manner of the embodiment of FIGS. 2 and 3. An orifice 229 restricts the flow of fluid being drawn on the vacuum line 224.

In FIG. 5, with the spool 256 in the down position, the piston chamber 235 is evacuated at the same time that the patient is evacuated via line 216. Then, when the patient catheter becomes occluded, the vacuum will increase in the patient line and the piston chamber 235 will see an increased vacuum and thus will cause the spool 256 to be shifted upwardly to the position therefor shown in FIG. 6, in which position the module 225 will be in a mode of intermitting operation in which the patient line 216 and piston chamber are both vented, in that the conduit 271 connects the vent conduit 272 and the patient conduit 216. The orifice restriction 229 in the vacuum supply line 224 ensures that the vacuum in the catheter (not shown) connected to patient line 216 will not be excessively high. Thus, it can be seen that, as long as the patient line 216 is flowing free, the piston chamber 235 does not have enough vacuum to shift the spool 256 to the vent position of FIG. 6.

It will be apparent from the foregoing that various modifications may be made in the use and operation of the apparatus of this invention, all within the spirit and scope of the invention as set forth in the appended claims.

What is claimed is:

1. An intermittent regulator for use in regulating the vacuum withdrawal of body fluids from a patient, comprising:
   (a) regulator housing having vacuum connection means for receiving a source of partial vacuum;
   (b) a patient connection means on said housing for connecting the patient to the vacuum connection means for delivering body fluids;
   (c) the regulator including a moveable piston in said housing;
   (d) the piston being movable in response to vacuum draw from the vacuum connection means, whereby the piston is moveable between first and second positions with the piston carrying a first spool movement means for movement therewith;
   (e) the spool carrying a second spool movement means for movement therewith and being movable in response to interaction between said first and second spool movement means when the piston is moved between said first and second positions, with the spool having conduit means for intermittently connecting the patient connection means to the vacuum connection means in response to movement of the spool, for intermittent withdrawal of body fluids from a patient.

2. The regulator of claim 1, wherein said first and second spool movement means each comprise magnets.

3. The regulator of claim 2, including:
   (f) timing means carried by said housing and vented to atmosphere, for controlling the movement of the piston and thereby controlling the intermittent withdrawal of body fluids;
   (g) diaphragm means separating the timing means from the conduit means;
   (h) whereby body fluids delivered to the regulator from a patient are isolated from the timing means.

4. The regulator of claim 2, wherein said piston and spool are free of physical contact with each other during their movements.

5. The regulator of claim 3, including means for adjusting the timing means for varying the intermittent movement of the piston.

6. The regulator of claim 5, wherein said adjusting means are isolated from the body fluids delivered to the regulator from a patient.

7. The regulator of any one of claims 1–3, including a manually engageable override on said spool, for allowing an optional manual override of the movement of the spool.

8. The regulator of any one of claims 1–3, including at least one stop on the spool, for limiting the movement of the spool in at least one direction.

9. The regulator of claim 8, including a pair of stops on the spool, for limiting movement of the spool in two directions.

10. The regulator of any one of claims 1–3, including means carried by the spool providing a visual indication of the position of the spool and thereby providing a visual indication of whether or not the spool is positioned for facilitating fluid flow from a patient.

11. The regulator of claim 9, wherein said means providing a visual indication comprise at least one stop means carried by the spool.

12. The regulator of any one of claims 1–2, wherein at least some of the conduit means on the spool are provided with solids-cutting sharp corners for severing solid particles entrained with fluid in the conduit, as the spool moves intermittently.

13. The regulator of claim 3, wherein said piston and spool are free of physical contact with each other during their movements, including means for adjusting the timing means for varying the intermittent movement of the piston, wherein said adjusting means are isolated from the body fluids delivered to the regulator from a patient, including a manually engageable override on said spool, for allowing an optional manual override of the movement of the spool, including a pair of stops on the spool, for limiting movement of the spool in two directions, including means carried by the spool providing a visual indication of the position of the spool and thereby providing a visual indication of whether or not the spool is positioned for facilitating a body fluid flow from a patient of the regulator, wherein said means providing a visual indication comprise at least one stop means carried by the spool, and wherein at least some of the conduit means on the spool are provided with solids-cutting sharp corners for severing solid particles entrained with fluid in the conduit, as the spool moves intermittently.

14. The regulator of any one of claims 1–2, wherein optionally openable porting is provided for applying vacuum to the piston at the same time vacuum is applied to a patient, whereby the regulator is converted from an intermittent mode of operation to a continuous mode of operation.

15. A regulator for use in regulating the vacuum withdrawal of body fluids from a patient, comprising:
   (a) regulator housing having vacuum connection means for receiving a source of partial vacuum;
   (b) a patient connection means on said housing for connecting the patient to the vacuum connection means for delivering body fluids;
   (c) the regulator including a moveable piston and a movable spool in said housing;

(d) the piston in a first position being normally essentially unvented to atmosphere when the patient connection means is substantially unoccluded, but being movable in response to vacuum draw from the vacuum connection means, whereby the piston is moveable from the first to a second position in which it is vented to atmosphere upon the patient connection means becoming substantially occluded, with the piston carrying a first spool movement means for movement therewith;

(e) the spool carrying a second spool movement means for movement therewith and being movable in response to interaction between said first and second spool movement means when the piston is moved between said first and second positions, with the spool having conduit means for connecting the patient connection means to the vacuum connection means when the patient connection means is substantially unoccluded and for disconnecting the patient connection means from the vacuum connection means while connecting the patient connection means to a vent opening in response to substantial occlusion of the patient connection means, by movement of the spool, for interrupting withdrawal of body fluids from a patient.

16. The regulator of claim 15, wherein said first and second spool movement means each comprise magnets.

17. The regulator of claim 16, including:

(f) timing means carried by said housing and vented to atmosphere, for controlling the movement of the piston and thereby controlling the intermittent withdrawal of body fluids;

(g) diaphragm means separating the timing means from the conduit means;

(h) whereby body fluids delivered to the regulator from a patient are isolated from the timing means.

18. An intermittent regulator for use in regulating the vacuum withdrawal of body fluids from a patient, comprising:

(a) regulator housing having vacuum connection means for receiving a source of partial vacuum;

(b) a patient connection means on said housing for connecting the patient to the vacuum connection means for delivering body fluids;

(c) the regulator including a vacuum responsive member and a movable valve in said housing;

(d) the vacuum responsive member being movable in response to vacuum draw from the vacuum connection means, whereby said member is moveable between first and second positions with the said member carrying a magnet means for movement therewith;

(e) the valve carrying magnet means for movement therewith and being movable in response to interaction between said vacuum responsive member and said valve when the vacuum responsive member is moved between said first and second positions, with the valve having conduit means for intermittently connecting the patient connection means to the vacuum connection means in response to movement of the valve, for intermittent withdrawal of body fluids from a patient.

* * * * *

UNITED STATES PATENT AND TRADEMARK OFFICE
CERTIFICATE OF CORRECTION

PATENT NO. : 6,228,056 B1                                                                 Page 1 of 1
DATED : May 8, 2001
INVENTOR(S) : John R. Boehringer, John Karpowicz, Michael I. Hegedus, Anthony Turchi It is certified that error appears in the above-identified patent and that said Letters Patent is hereby corrected as shown below:

<u>Column 7,</u>
Line 45, after piston insert --; and a movable spool --.

Signed and Sealed this

Nineteenth Day of February, 2002

Attest:

JAMES E. ROGAN
Attesting Officer        Director of the United States Patent and Trademark Office